(12) United States Patent
Chang et al.

(10) Patent No.: US 7,680,629 B2
(45) Date of Patent: Mar. 16, 2010

(54) SYSTEM AND METHOD FOR PROVIDING NOTES IN MEASUREMENT DEVICES

(75) Inventors: Chin-Hsiung Chang, Tai-Chung (TW); Fu-Chung Yen, Plano, TX (US)

(73) Assignee: FEGO Precision Industrial Co., Ltd., Tai-Chung (TW)

( * ) Notice: Subject to any disclaimer, the term of this patent is extended or adjusted under 35 U.S.C. 154(b) by 264 days.

(21) Appl. No.: 11/847,682

(22) Filed: Aug. 30, 2007

(65) Prior Publication Data

US 2009/0063098 A1    Mar. 5, 2009

(51) Int. Cl.
*G06F 17/40* (2006.01)
(52) U.S. Cl. ...................................... 702/187
(58) Field of Classification Search .............. 702/187, 702/182–185
See application file for complete search history.

(56) References Cited

U.S. PATENT DOCUMENTS

| 6,893,396 B2* | 5/2005 | Schulze et al. .......... 600/300 |
| 2008/0134074 A1* | 6/2008 | Cable .................... 715/771 |

\* cited by examiner

*Primary Examiner*—Edward Raymond
(74) *Attorney, Agent, or Firm*—Locke Lord Bissell & Liddell LLP; Zunxuan "Digger" Chen; Hong "Tracy" Zou

(57) ABSTRACT

A measurement device with capabilities of note taking. The measurement device comprises at least one measurement component, adapted to perform measurement in at least one measuring event of the measurement device; a note control component, adapted to obtain and record at least one note input with respect to the at least one measuring event; and a Central Processing Unit (CPU), adapted to link the at least one note with the at least one measuring event.

20 Claims, 9 Drawing Sheets

BP.txt

| yyyy-mm-dd hh:mm | sys | dia | HR | S1 | S2 | S3 | S4 | S5 | S6 | S7 | S8 | TN | VN |
|---|---|---|---|---|---|---|---|---|---|---|---|---|---|
| 2007-07-08 08:34 | 124 | 78 | 68 | 1 | 0 | 8 | 0 | 1 | 1 | 0 | 0 | 1 | 1 |
| 2007-07-08 20:12 | 128 | 81 | 73 | 0 | 0 | 5 | 0 | 0 | 0 | 2 | 0 | 0 | 0 |
| 2007-07-09 08:15 | 124 | 78 | 68 | 2 | 0 | 6 | 0 | 1 | 1 | 0 | 0 | 0 | 0 |
| 2007-07-09 21:01 | 124 | 78 | 68 | 0 | 0 | 2 | 0 | 0 | 0 | 3 | 0 | 0 | 0 |
| 2007-07-10 08:56 | 124 | 78 | 68 | 0 | 0 | 0 | 0 | 1 | 1 | 0 | 0 | 1 | 1 |
| 2007-07-10 21:08 | 124 | 78 | 68 | 0 | 0 | 0 | 0 | 0 | 0 | 2 | 0 | 0 | 0 |
| 2007-07-11 08:25 | 124 | 78 | 68 | 0 | 0 | 0 | 0 | 1 | 1 | 0 | 0 | 0 | 1 |
| 2007-07-11 20:56 | 124 | 78 | 68 | 0 | 8 | 0 | 3 | 0 | 0 | 0 | 0 | 1 | 0 |

S1: Hungry  S5: Take medicine  TN: Text Note
S2: Bad mode  S6: Take caffeine  VN: Voice Note
S3: Sleepy  S7: Take alcohol
S4: Dizzy  S8: After exercise

FIG. 3

Notes.txt

```
yyyy-mm-dd hh:mm Notes
2007-07-08 08:34 I feel uncomfortable this morning. Bone sore and fatigue.
2007-07-10 08:56 Get better today. Felt very hungry. I ate a lot before BP measurement.
2007-07-11 20:56 Got hurt this afternoon. I took a long nap before BP measurement.
```

FIG. 4

Voice Notes

Notes_2007-07-08_0834.snd ⟶ * Sound files are in binary
Notes_2007-07-10_0856.snd ⟵ format and when printout will
Notes_2007-07-11_0825.snd ⟵ look like

The links among BP.txt, Notes.txt and Voice Notes

Notes.txt

```
yyyy-mm-dd hh:mm Notes
2007-07-08 08:34 I feel uncomfortable this morning. Bone sore and fatigue.
2007-07-10 08:56 Get better today. Felt very hungry. I ate a lot before BP measurement.
2007-07-11 20:56 Got hurt this afternoon. I took a long nap before BP measurement.
```

Voice Notes

Notes_2007-07-08_0834.snd

Notes_2007-07-10_0856.snd

Notes_2007-07-11_0825.snd

BP.txt

```
yyyy-mm-dd hh:mm sys dia HR S1 S2 S3 S4 S5 S6 S7 S8 TN VN
2007-07-08 08:34 124 78 68 1 0 8 0 1 1 0 0 1  1  1
2007-07-08 20:12 128 81 73 0 0 5 0 0 0 2 0 0  0  0
2007-07-09 08:15 124 78 68 2 0 6 0 1 1 0 0 0  0  0
2007-07-09 21:01 124 78 68 0 0 2 0 0 0 3 0 0  0  0
2007-07-10 08:56 124 78 68 0 0 0 0 0 1 1 0 0  1  1
2007-07-10 21:08 124 78 68 0 0 0 0 0 0 2 0 0  0  0
2007-07-11 08:25 124 78 68 0 0 1 0 0 1 0 0 0  1  1
2007-07-11 20:56 124 78 68 0 8 0 3 0 0 0 0 0  1  0
```

FIG. 6

SYSTEM AND METHOD FOR PROVIDING NOTES IN MEASUREMENT DEVICES

CROSS-REFERENCE TO RELATED APPLICATIONS

This application is related to: U.S. application Ser. No. 11/847,842, filed currently with the present application on Aug. 30, 2007, entitled "BLOOD PRESSURE MEASUREMENT DEVICE", by Chin-Hsiung Chang and Fu-Chung Yen; and U.S. application Ser. No. 11/848,025, filed currently with the present application on Aug. 30, 2007, entitled "SYSTEM FOR INTEGRATING AND MANAGING HEALTH RELATED INFORMATION", by Chin-Hsiung Chang and Fu-Chung Yen.

TECHNICAL FIELD OF THE INVENTION

The present invention relates generally to electronic devices, and, more particularly, to a system for providing notes in measurement devices.

BACKGROUND OF THE INVENTION

A measurement device is a device that may provide functions for measuring one or more specific signals. It is not unusual that many signals to be measured may vary with various influential factors. For example, blood pressure of a subject may vary before or after the subject performs exercises. Taking notes of these influential factors together with the measured signals are helpful in explaining and understanding the measurement and results. Notes may also be used to record background information for using a measurement device, observations during or description of a measurement, or any other information that is related to the measurement and measurement results.

However, conventional measurement devices lack capabilities to take notes with respect to a measurement in real-time and to manipulate the notes taken, and do not provide an integrated mechanism to take the notes. In one example, medical doctors usually face problems of lacking an integrated mechanism to help them take notes when they perform diagnosis or treatment on patients using a medical device. For example, when a doctor performs ultrasonography (ultrasonic image) on a patient, the doctor captures images as he finds what he is looking for. Since conventional devices do not provide convenient ways to take notes in real-time for describing the images just captured, the doctor needs to stop taking images, and to take notes off-line. The pauses waste time of both the doctor and the patient. More importantly, the doctor might miss critical moments to capture the best images since the human body status is changing all the time. Some of the conventional devices for performing ultrasonography may have a keyboard provided, however, a doctor still needs to stop taking images for keying in the notes, or to ask someone else to take the notes for him when he is taking the images.

In an alternative example, users of healthcare devices face similar problems. They need a system to help them take notes when they use the healthcare devices to measure physical or physiological parameters, such as blood pressure, heart rate, body fat/weight, or blood sugar, etc. For example, when a user measures blood pressure using a blood pressure meter, the blood pressure level may change with various physical or environmental conditions, such as blood pressure of the user may vary if the user is very hungry, or right after the user does exercises, etc. However, conventional blood pressure measurement devices may not have capabilities to take notes of measurement conditions and store the notes together with the measured blood pressure values. The notes, if available, will be significantly helpful for doctors in providing diagnosis or treatment of hypertension and other heart related diseases.

In another example, a fitness trainer may have needs of taking notes when designing a fitness training program on a fitness apparatus that fits a fitness trainee most appropriately. The trainee may perform exercises on the fitness apparatus according to the designed fitness training program. For design of the fitness training program, the trainer may not only need to have knowledge of health conditions and requirements of the trainee, but also needs to know how the fitness training program works on the trainer. Conventional fitness apparatuses may perform some measurement and calculations, and record workouts such as speed, time, calorie consumed, etc. during the exercise, which may be used by the trainer in the design of the fitness training program. Other information, however, such as the trainees' feeling, observations, or the trainee's posture during the exercise may not be measured or recorded. This information may be recorded by way of taking notes during the exercise. But, a trainer may not be with each trainee all the time taking notes. Some fitness training center may use separated instruments to record the information.

Other measurement device may also have a need of a real-time note taking mechanism. For example, an oscilloscope may be used for measuring electronic signals to understand the signal waveforms for signal quality. Hardware engineers often use oscilloscopes to troubleshooting circuit boards. If a problem occurred to a complex circuit board, an engineer sometimes needs to measure, record, and compare signals measured from many places of the circuit board in order to diagnosis the problem. With the number of signals measured increasing, a flexible and real-time note-taking mechanism may be very helpful for the engineer to replay, review, and compare a large number of signals to identify the problem.

Therefore, there is a need for a system that provides an integrated mechanism for providing notes in real-time with respect to measurements of a measurement device. There is also a need for a system that provides capabilities to manipulate notes provided with respect to measurements of a measurement device.

SUMMARY OF THE INVENTION

A measurement device with capabilities of note taking. The measurement device comprises at least one measurement component, adapted to perform measurement in at least one measuring event of the measurement device; a note control component, adapted to obtain and record at least one note input with respect to the at least one measuring event; and a Central Processing Unit (CPU), adapted to link the at least one note with the at least one measuring event.

A system of note taking from measurement devices is also provided. The system comprises a measurement device, performing at least one measuring event; means for inputting at least one note with respect to the at least one measuring event; and means for manipulating the at least one note. The measurement device is adapted to obtain the at least one note with respect to the at least one measuring event, to link the at least one note with the at least one measuring event, and to store the at least one note.

The following description and drawings set forth in detail a number of illustrative embodiments of the invention. These embodiments are indicative of but a few of the various ways in which the present invention may be utilized.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 3 is a diagram depicting an embodiment of a file for storing blood pressure measurement data and numeral notes according to the present invention;

FIG. 4 is a diagram depicting an embodiment of a file for storing text notes according to the present invention;

FIG. 5 is a diagram depicting an embodiment of files for storing audio notes according to the present invention;

FIG. 6 is a diagram depicting an embodiment of links between the blood pressure measurement data, numeral notes, text notes and audio notes according to the present invention;

DETAILED DESCRIPTION

The following discussion is presented to enable a person skilled in the art to make and use the invention. The general principles described herein may be applied to embodiments and applications other than those detailed below without departing from the spirit and scope of the present invention as defined herein. The present invention is not intended to be limited to the embodiments shown, but is to be accorded the widest scope consistent with the principles and features disclosed herein.

A measurement device may be a device that provides functions for measuring one or more specific measurement signals. A measurement device may include, but not limited to a health related measurement device, such as a healthcare device—e.g., a blood sugar reader, a medical treatment or diagnosis device—e.g., an electrocardiographic monitor, a fitness apparatus—e.g., a treadmill, an environmental measurement or control device—e.g., a humidity reader, a thermometer, or a dust density meter, etc.; and many other measurement devices used in various fields. In the following descriptions and embodiments, health related measurement devices are used for description conveniences. However, the use of the health related measurement devices are not to be construed as limiting terms. The present invention may be applied to any measurement devices without departing the spirit and scope of the present invention.

Figure 1:
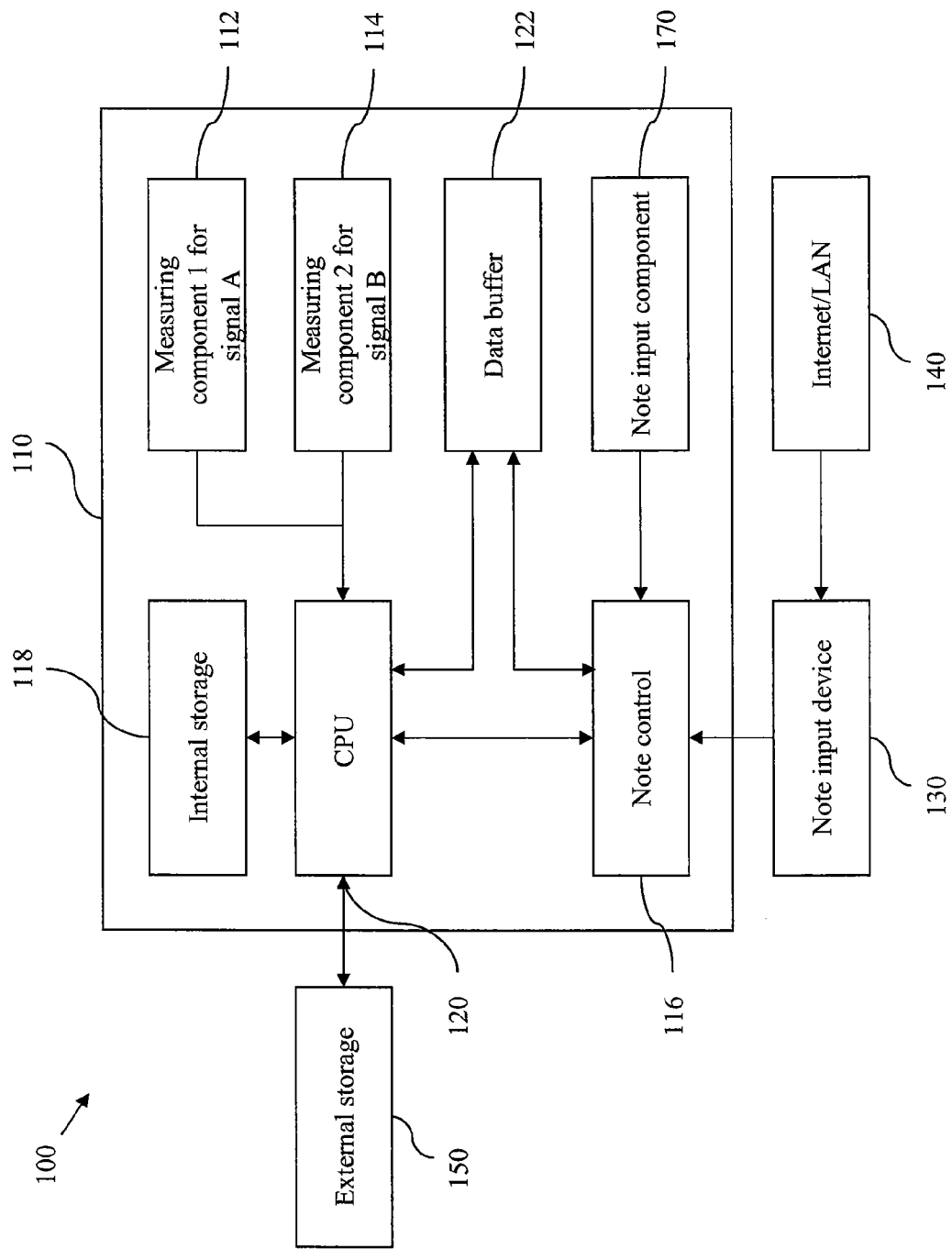
FIG. 1 is a diagram depicting an embodiment of structures of a system for providing notes in a health related measurement device according to the present invention.

Referring to FIG. 1, an embodiment of structures of a system (100) for providing notes with respect to measured signals in a health related measurement device is illustrated. The system (100) may provide measurement of health related signals, e.g., signal A and signal B, and note(s) taking with respect to each measuring event for measuring the signal A and/or B. The note(s) may be linked with a corresponding measuring event and saved. The linking may automatically correlate records of note(s) and measured signals in a corresponding measuring event, and thus the measured signals and note(s) in the measuring event, which may be obtained at different time, may be taken as an integrated data record for the measuring event. Using the link, a note with respect to a measuring event may be easily tracked by the measuring event, or a measuring event may be traced back by a corresponding note. The linking facilitate manipulation of the notes taken for a particular event, such as view, or edit, a note for a particular measuring event.

The system (100) may comprise a health related measurement device (110), measuring health related signals; and a note input device (130) connected with the health related measurement device (110), for inputting notes corresponding to a measuring event.

The health related measurement device (110) may further comprise a measuring component 1 (112) and a measuring component 2 (114), for measuring the signal A and signal B, respectively; a note control component (116) for receiving and recording, etc. notes input via the note input device (130); an internal storage component (118) for storing data involved in the system (100), including the signal A and/or B measured, notes input, and other applicable data; a Central Processing Unit (CPU) (120) for centrally control and monitoring of the system (100); and a data buffer (122) for buffering data involved in the system (100).

The measured signals and corresponding notes taken in a measuring event may be placed in the data buffer (122) when available, and the CPU (120) may process the data stored in the data buffer (122). For example, the CPU (120) may generate links between measured signals and corresponding notes, set up flags for the links, and/or save the processed data in the internal storage component (118) or other storage devices. The note control component (116) and the CPU work together to enable notes to be taken and recorded in an integral manner as measurement is performed by the health related measurement device (110).

The note input device (130) may be connected with an Internet or a Local Area Network (LAN) (140), through which notes may be input remotely into the health related measurement device (110). The system (100) may further comprise a storage device (150) outside the health related measurement device (110), for storing any data involved in the system (100). The external storage device (150) may communicate with the health related measurement device (110), exchanging data involved in the system (100). The external storage device (150) may also be used to enlarge storage capacity of the health related measurement device (110), but may be optional.

The health related measurement device (110) may be an electronic device or apparatus that may provide measurement of any health related signals. Such a health related measurement device may include, but not limit to, a healthcare device, a medical diagnostic or treatment apparatus, a fitness apparatus, and an environmental measurement or control device, etc. Examples of a health related measurement device (110) may be a blood pressure measurement device, a body fat reader, a treadmill, and a stepper, etc. Examples of an environmental measurement or control device may include a humidity reader, thermometer, an air conditioner, or a dust density meter, etc. Signals measured by the health related measurement device (110) may include blood pressure, body fat, body weight, heart rate, blood cholesterol, blood sugar, calories consumed, electrocardiogram (ECG), etc. Some health related measurement devices may provide measurement of more than one signal, e.g., a blood pressure meter measures both blood pressure and heart rate of a subject.

The external storage device (150) may be removably connected with the health related measurement device (110) when needed, and the connection may be by wire or wireless. One example of the external storage device (150) may be a non-volatile memory product, such as a USB flash drive, a memory stick, etc. To connect with the external storage device (150), the health related measurement device (110) may need to have or provide a wire or wireless interface. For example, in the case of a USB flash drive as an example of the external storage device (150), the health related measurement device (110) may need to have a built-in USB port or provide a USB hub.

A health related measurement device, e.g., (110) may not have the internal storage device (118). In this case, the measured signals A and/or B and corresponding notes taken may be stored in the connected external storage device (150), or a computer connected with the health related measurement device (110).

A note may be used to record information that is related to measurement, and consequently, measured signals of a measurement device, e.g., the health related measurement device (110). It is not unusual that a signal measured by a measurement device may vary with respect to various factors. In the case of the blood pressure measurement device (110), these factors may include physical or physiological parameters and/or conditions of a subject, e.g., taking medications, drinking coffee, or having headache, etc; environmental parameters, e.g., room temperature or humidity, etc., and many other factors that may affect the measurement of blood pressure of a subject. For instance, blood pressure of a subject may vary if the subject is sick, drinking alcohol, doing exercises, hungry, or if the blood pressure is measured in a room with very high humidity, etc. These factors may be referred as measurement states, and may be recorded by way of taking notes.

A note may also include information that may help understand background of a measuring event and help use the measurement results. For example, a note may record reasons why a measurement of a health related signal is performed; or a note may record descriptions about a measuring event, e.g., description of professional observations, or feelings of a measurement subject, etc. A note may further record professional advices and/or opinions, suggested plans, e.g., treatment or prescriptions, or other supplemental information about a measuring event.

Recording and storing of the information provides supplementary information for measurement of a measurement device, which may produce a more complete and meaningful picture of measurement in a measuring event, and make the measurement more useful.

The note input device (130) may be a keyboard, a mouse, a pen tablet, a computer, a camcorder, a camera, or a microphone, etc., or an equivalent that may be used to input notes, and may be integrally or removably connected with the health related measurement device (110). An interface may be provided by the health related measurement device (110) for connecting with the note input device (130), which may vary with the note input device (130) to be connected. For example, the health related measurement device (110) may have a USB port to connect with a computer or a keyboard, an AUX port to connect with a wired microphone; or a wireless interface to connect with a computer or wireless microphone; etc.

There may be more than one note input device (130) connected with the health related measurement device (110), and a user may conveniently choose one he/she thinks appropriate to take notes. In this case, the health related measurement device (110) needs to provide interface(s) compatible with each of the note input devices. That is, the health related measurement device (110) may provide one or more interfaces such that the health related measurement device (110) may be connected with various note input devices flexibly to take notes as needed.

The health related measurement device (110) may further comprise one or more built-in note input component(s) (170). A built-in note input component (170) of the health related measurement device (110) may be a built-in microphone, or one or more operational keys for operating the health related measurement device (110), e.g., buttons, rotary switches, etc. For example, a user may take audio notes with respect to his/her blood pressure measurement just measured by a blood pressure measurement device using a built-in microphone; or the user may input notes by operating buttons of the blood pressure measurement device. Therefore, in system (100), a health related measurement device (110) may have one or more built-in note input component(s) and/or one or more externally connected note input device(s).

A note may be taken and stored in various formats, which include, but not limited to, audios, videos, images, texts, etc, and the formats to be used may depend on the note input devices (130) or the note input components (170). Notes in different formats with respect to one measuring event may be saved in separate files, but linked together with the measuring event. A note taken in one type of format may also be converted to another format. For instance, a doctor may record his/her observations as he/she is performing ultrasonography using a microphone. The recorded voice information may then be converted to texts and saved as a text note.

Some information taken as notes may be input and saved in a simple way. For example, some physical or physiological states of a measurement subject may be represented simply by "yes" or "no", such as whether the subject has taken medications, or whether the subject has done exercises. In this case, numerals "1" and "0" may be used to record the information, respectively. If the information may be classified in severity or degrees, then more numerals may be used. The numerals corresponding to severity or degrees of a measurement state may be predefined and/or configurable. These notes may be referred to as "numeral notes".

Table 1 shows an embodiment of numeral notes taken for a user measuring his/her blood pressure. In this embodiment, the user took some blood pressure reduction medications, four cups of coffee, and felt hungry before measuring his/her blood pressure. The user may input numeral notes by operating operational keys of his/her blood pressure measurement device before starting to measure his/her blood pressure. The "notes" column in Table 1 corresponding to the "Take medication" is recorded as 1, indicating that the user took medications in regular doses; and the "notes" column corresponding to "Take coffee" is recorded as 5, since the user took a lot of coffee. The "notes" column corresponding to "Dizzy" is 0 since the user did not feel any dizzy.

TABLE 1

| States | Notes |
| --- | --- |
| Take medication | 1 |
| Take coffee | 5 |
| Dizzy | 0 |

In this embodiment, the user also felt hungry before measuring his/her blood pressure. If this measurement state of "hungry" may not be recorded as a numeral note, the user may key in this measurement state in texts by operating operational keys of the blood pressure measurement device, or by operating a keyboard connected with the blood pressure measurement device. In an alternative embodiment, the user may record a audio note using a built-in microphone of the blood pressure measurement device describing this measurement state.

A note may be taken corresponding to each measuring event. A note may be input before, during or after measurement in a measuring event of the health related measurement device (110), and then linked and saved with a corresponding measuring event. For instance, in one measuring event, a user may enter numeral notes of taking medication '1' and taking coffee '5' before measuring blood pressure; then the user may take audio notes during the measurement or enter text notes after the measurement. All notes may be linked with the measuring event, and stored in the internal storage component (118) and/or external storage device (150).

There are various methods to link notes with a corresponding measuring event. In one embodiment, each measuring event may be assigned a unique ID, and notes corresponding to measuring event may be linked using this ID. In another embodiment, notes corresponding to a measuring event may be synchronized with the measuring event, i.e. a timestamp may be used to link a note with a measuring event. The timestamp may be a time at which a measuring event occurs.

Figure 2:
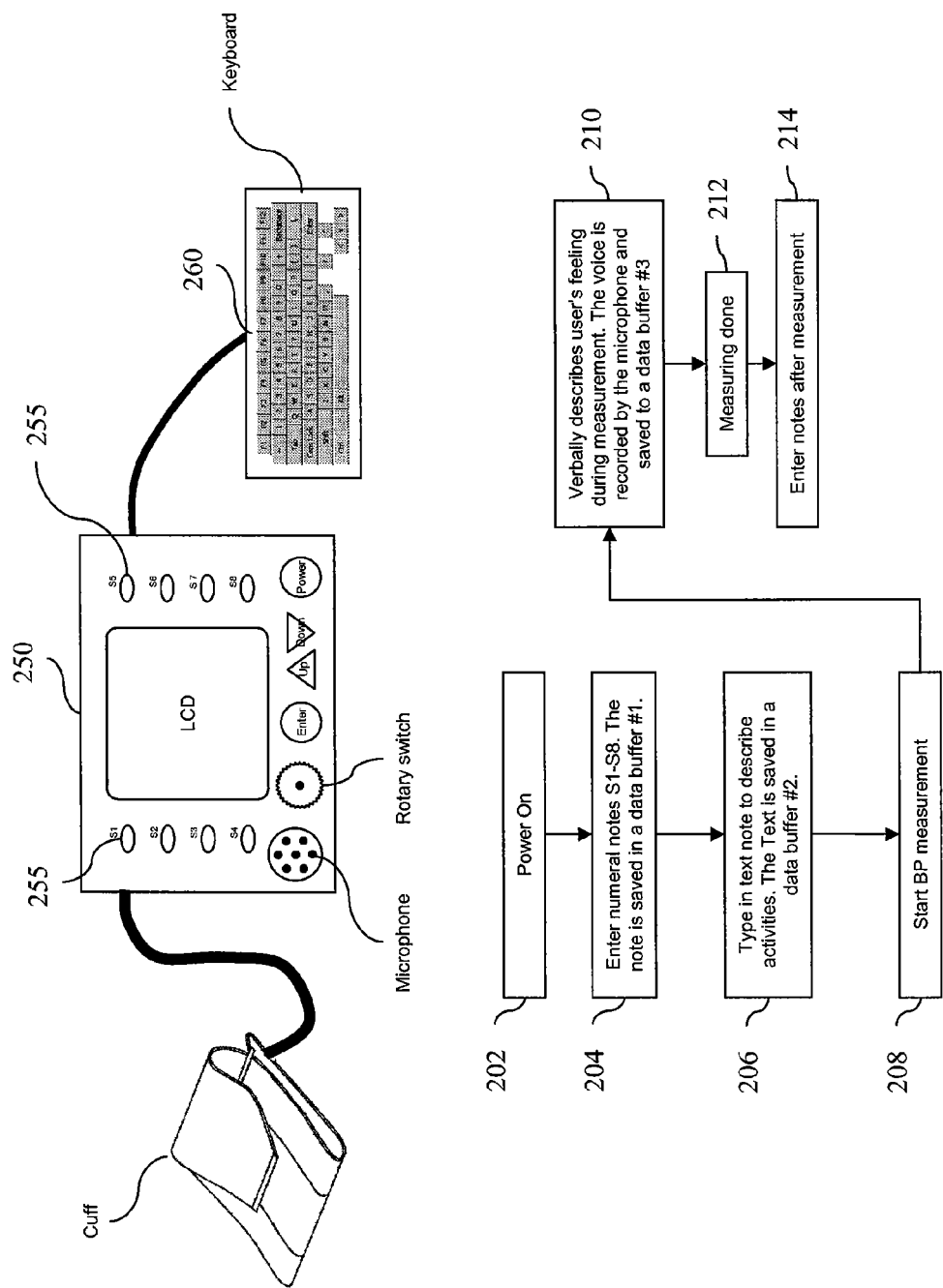
FIG. 2 is a flowchart depicting an embodiment for providing notes in a blood pressure measurement device according to the present invention.

FIG. 2 is a flow chart illustrating one embodiment of note taking and linking in a blood pressure measurement device according to the present invention. In this embodiment, date and time for measuring blood pressure in one measuring event, which are referred as measuring timestamp, are used to link each note with a blood pressure measuring event. Once power on a blood pressure measurement device (250) in step (202), a user may take some notes before measuring his/her blood pressure using the blood pressure measurement device. The blood pressure measurement device (250) provides a plurality of operational keys, e.g., buttons (255), for a user to input numeral notes, e.g., some measurement states, such as those states described in Table 1, by simply pressing corresponding buttons. Eight buttons (255) are illustrated in FIG. 2, each representing a different measurement state (S1-S8) for the blood pressure measurement, as shown in Table 2. In step (204), the user may select one or more measurement states by pressing one or more buttons (255). The blood pressure measurement device (250) may receive the selection of the measurement states and save the selection in a data buffer #1.

TABLE 2

| States | Description |
|---|---|
| S1 | Hungry |
| S2 | Bad mode |
| S3 | Sleepy |
| S4 | Dizzy |
| S5 | Take medication |
| S6 | Take caffeine |
| S7 | Take alcohol |
| S8 | After exercises |

In step (206), the user may also connect a keyboard (260) with the blood pressure measurement device (250), and type in some text notes, e.g., describing his feeling, before the blood pressure measurement. The typed-in texts may be displayed on a screen of the blood pressure measurement device (250), and the text notes may be saved in a data buffer #2.

The user may begin to measure his/her blood pressure in step (208) by operating an operational key on the blood pressure measurement device (250). During the measurement of blood pressure, the user may verbally describe his/her feeling using a built-in microphone in step (210). The audio notes may be recorded and saved in a data buffer #3.

After the blood pressure measurement is finished in step (212), the user may also enter more notes in step (214), with respect to the blood pressure measuring event just occurred, such as comments, observations about this blood pressure measuring event. These notes taken after the measuring event may be linked with the blood pressure measuring event by identifying the measuring timestamp of the measuring event.

The blood pressure measurement device (250) may store the blood pressure measurement data in the data buffer #1, and link the notes saved in the data buffer #1, #2 and #3 with the blood pressure measuring event by the measuring timestamp. There may be various ways to store data involved in a measuring event and corresponding notes, and link the measuring event with the corresponding notes. In this embodiment, one file may be used to store blood pressure measurement data and the numeral notes entered though the buttons (255) of different measuring events, and another file may be used to store text notes corresponding to different measuring events. Each audio note corresponding to one particular measuring event may be saved into a separate file due to the relative large size of an audio file.

The blood pressure measurement data and numeral notes entered by selecting buttons (255) of the blood pressure measurement device (250) are saved into one file, e.g., bp.txt, as shown in FIG. 3. The blood pressure measurement data and the corresponding numeral notes resulted from each measuring event may be organized and identified by a measuring timestamp of each measuring event, i.e., the "yyyy-mm-dd" and "hh:mm" columns in FIG. 3. Blood pressure measurement data of one measuring event is distinguished from that of other measuring events by measuring stamps. Blood pressure measurement data of multiple measuring events occurred at different timestamps may be sorted and arranged by the measuring timestamps in an ascending or descending order. As illustrated in FIG. 3, all blood pressure measurement data is sorted in an ascending order, for example, blood pressure measurement data and numeral notes for 2007-07-11 at 20:56 is appended after that for 2007-07-11 at 08:25.

Blood pressure measurement data for each measuring event may include a systolic pressure value, a diastolic pressure value, and a heart rate value, which are recorded in columns "sys", "dia" and "HR", respectively, in FIG. 3. Columns "S1" to "S8" represent numeral notes selected using the buttons (255), where "1" for a corresponding measurement state means that the measurement state is selected; "0" means not selected; and a numeral larger than 1 means that the measurement state is selected, and has a different level of severities. For example, columns "S3", "S5" and "S6" has a value 8, 1, and 1, respectively, for a measuring event taken place on 2007-07-08 at 08:34, which represents that the user felt very sleepy (severity 8), and took some medications (severity 1) and caffeine (severity 1) when measuring his/her blood pressure at that time. Thus in this embodiment, the numeral notes concerning measurement states with respect to a measuring event are directly linked with blood pressure measurement data of a corresponding measuring event by a measuring timestamp of the measuring event.

To link other corresponding notes, e.g., text notes and audio notes, with the blood pressure measuring event, two flags, i.e., columns "TN" and "VN" in FIG. 3, are included in the BP.txt file, indicating whether there exist text notes or audio notes with respect to the blood pressure measuring event of a specific date and time. If the value of the "TN" or "VN" of a specific date and time is "1", then text or audio notes exist for the blood pressure measurement taken at the specific date and time. Otherwise, i.e., if the "TN" or "VN" has a value of "0", there is no notes related to the blood pressure measuring event. When a text note or a audio note is removed, the value of a corresponding flag may be updated accordingly.

Figures 4, 5:
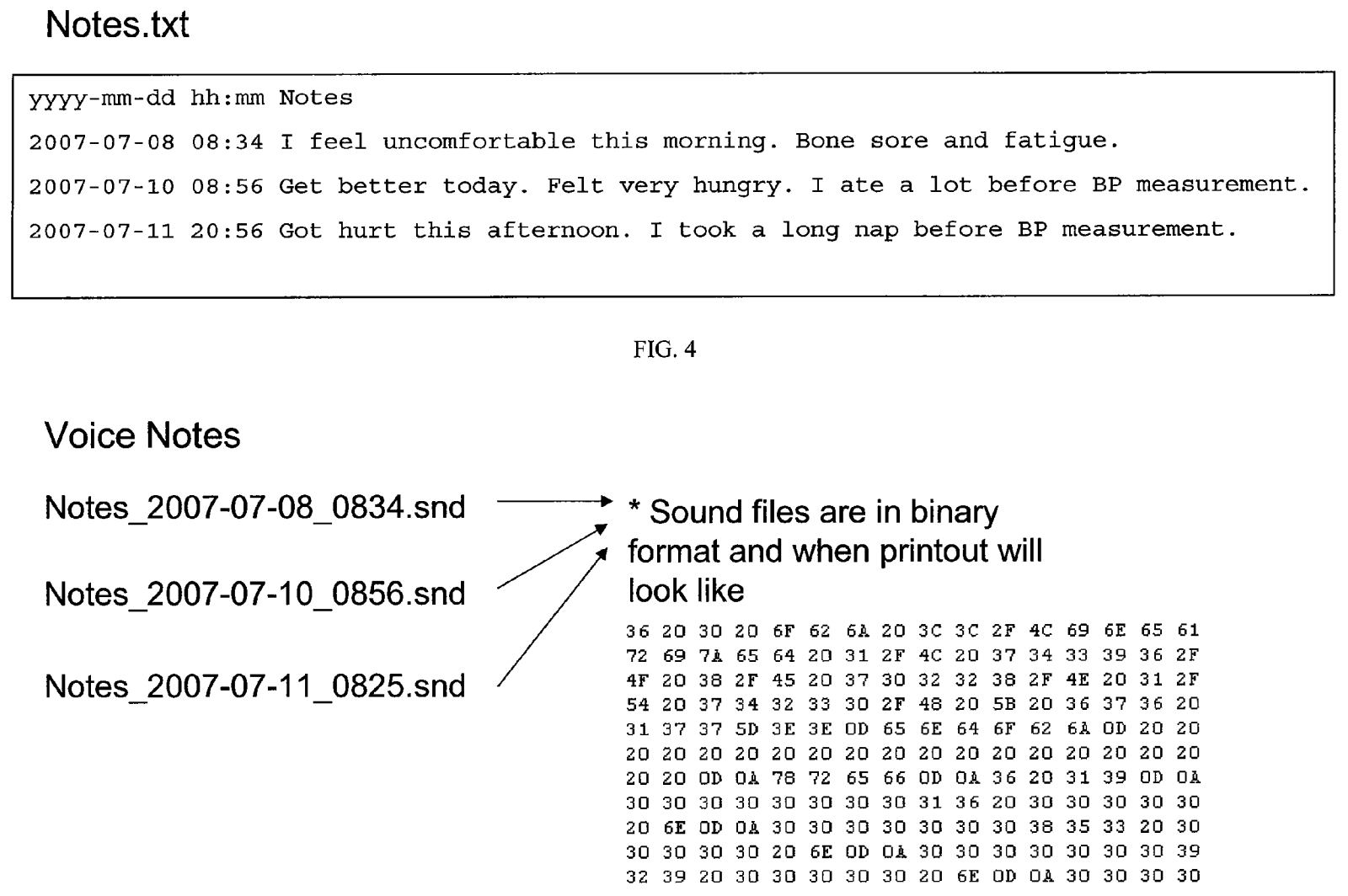

All text notes of different measuring events may be saved into one file, e.g., "Notes.txt" file shown in FIG. 4. The text notes may also be identified and organized by measuring timestamps of corresponding measuring events. Text notes corresponding to the same measuring event, e.g., two text notes are input before and during measurements in one measuring event, respectively, may be combined together and identified by a measuring timestamp of the measuring event. For instance, in FIG. 4, a blood pressure measuring event occurred at a date and time of "2007-07-10, 08:56" has three corespondent text notes that are combined together and stored, i.e., "Get better today", "Felt very hungry", and "I ate a lot before BP measurement". The text notes for different measuring events may also be sorted or arranged by measuring timestamps. Thus, text notes and blood pressure measurement data are correlated by using a measuring timestamp of a blood pressure measuring event. Each audio note may be saved into one file, with date and time of a measuring event included in the file name, such as the file "Notes__2007-07-08__0834.snd" in FIG. 5.

Referring to FIG. 6, links between each blood pressure measuring event, the corresponding numeral notes, text notes and audio notes in FIGS. 3, 4 and 5 are illustrated. The text notes and audio notes are linked with a particular blood pressure measuring event by measuring timestamp, e.g., date and time when this particular blood pressure measuring event occurs, with flags TN and VN indicating existence of a text or audio note corresponding to the particular blood pressure measuring event. The flags and numeral notes with respect to each measuring event are saved together with the measurement data of each blood pressure measurement event.

The system (100) back in FIG. 1 may further comprise a computer to manipulate—i.e., view, add, delete, edit, print, backup, etc.—notes recorded with respect to each measuring event of the health related measurement device (110). The role of the computer may also be played by a Personal Digital Assistant (PDA), or an equivalent device that may allow a user to manipulate notes taken. Software may be provided to enable the manipulation of notes. FIG. 7 illustrates an embodiment for displaying notes with respect to blood pressure measurement data using a user interface on a computer screen. Systolic pressure, diastolic pressure and heart rate are shown by dotted charts in section (710), indicating a subject's blood pressure trend during a period from Feb. 01, 2007 to Apr. 11, 2007. The x-axis represents the date and time. The icon (720) shown at a particular point along the x-axis indicates that there is a note existent with respect to a blood pressure measuring event occurred at the particular point, i.e., date and time. Double click the icon (720) may display content of the note on the screen, as shown by the small window (730) in FIG. 7B.

Figure 7A:
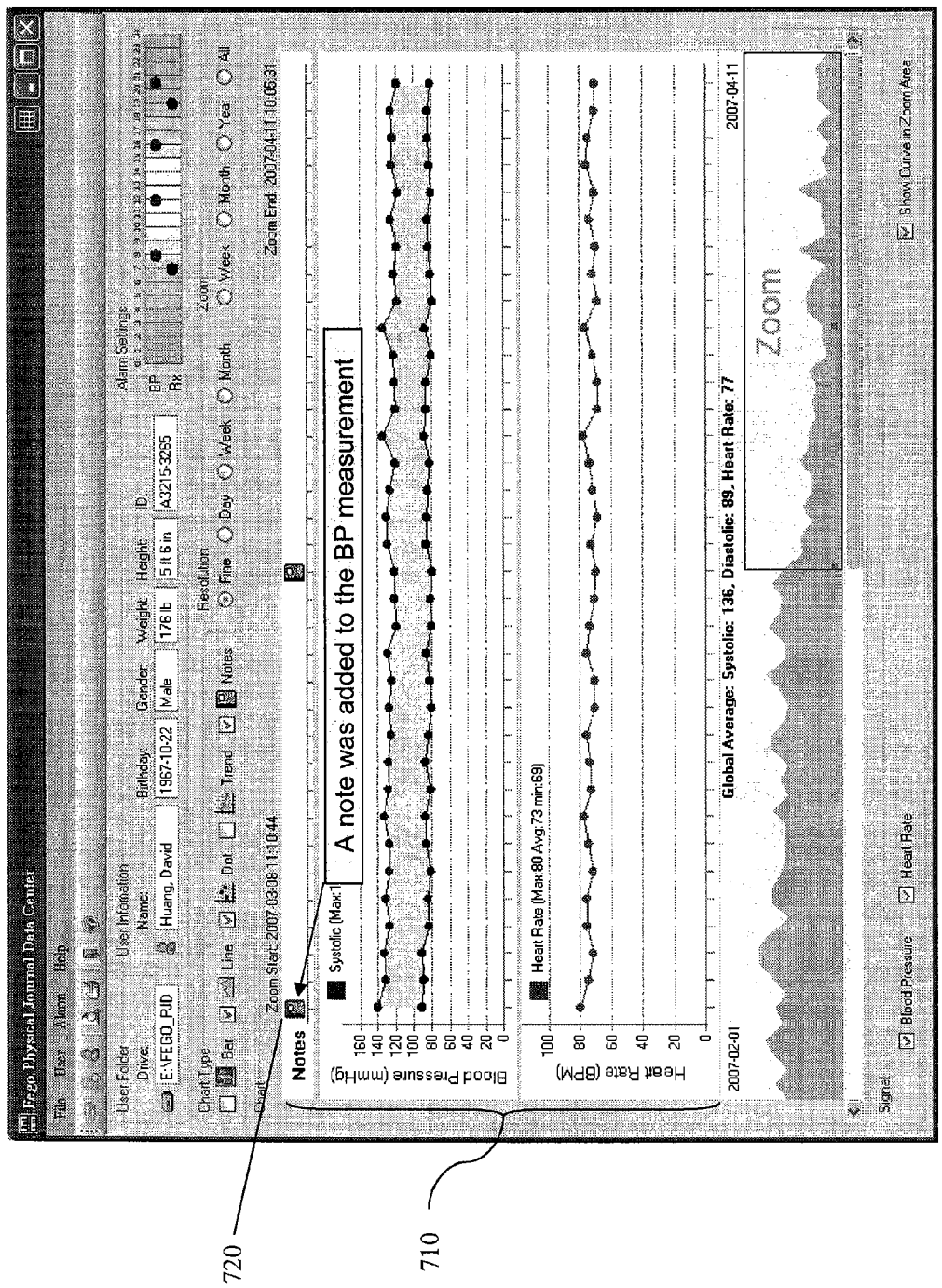
FIGS. 7A and 7B are diagrams depicting an embodiment for displaying a note with respect to a blood pressure measuring event on a computer screen according to the present invention.
Figure 7B:
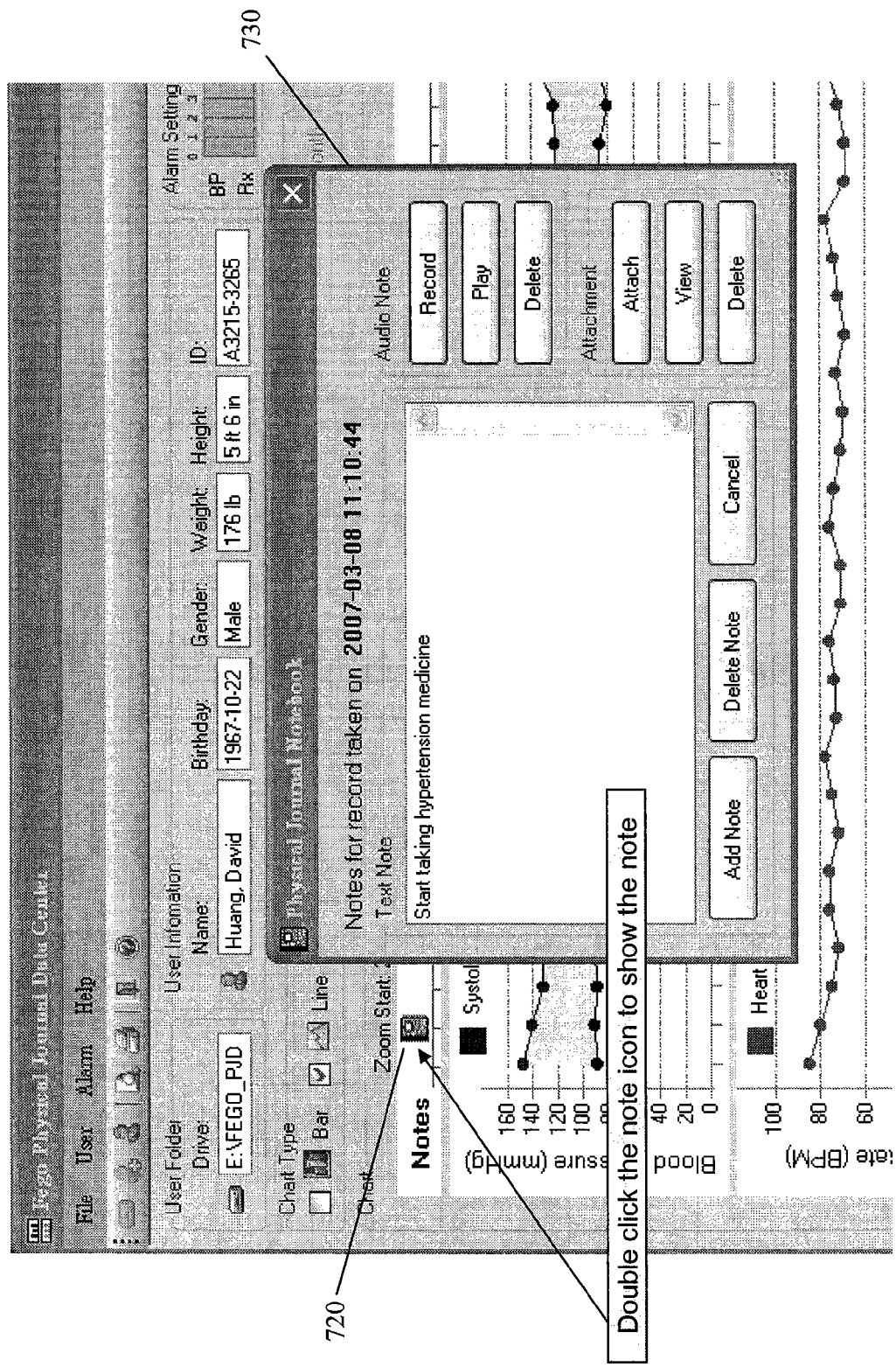
Figure 7C:
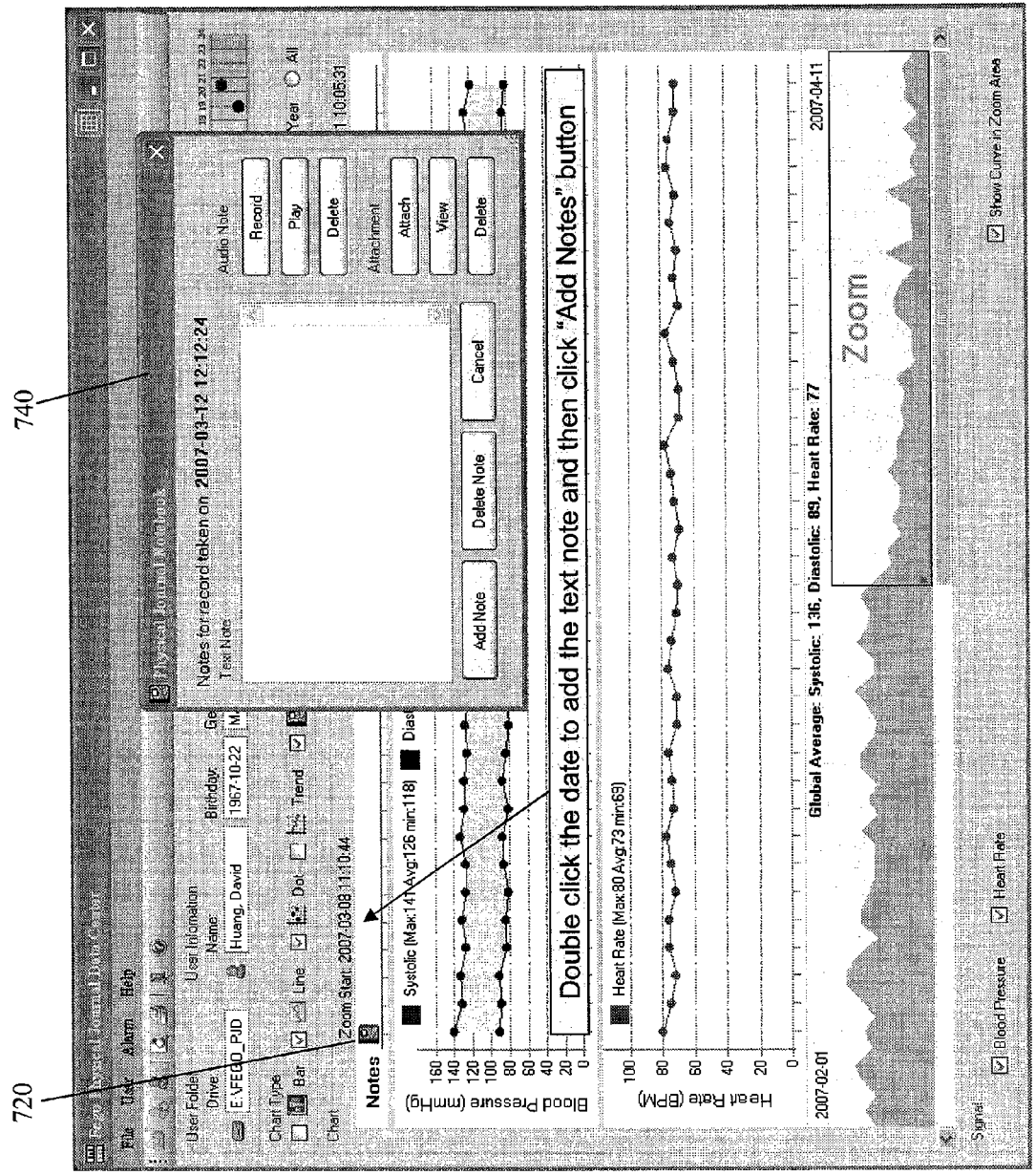
FIGS. 7C and 7D are diagrams depicting an embodiment for adding a note with respect to a blood pressure measuring event on a computer screen according to the present invention.
Figure 7D:
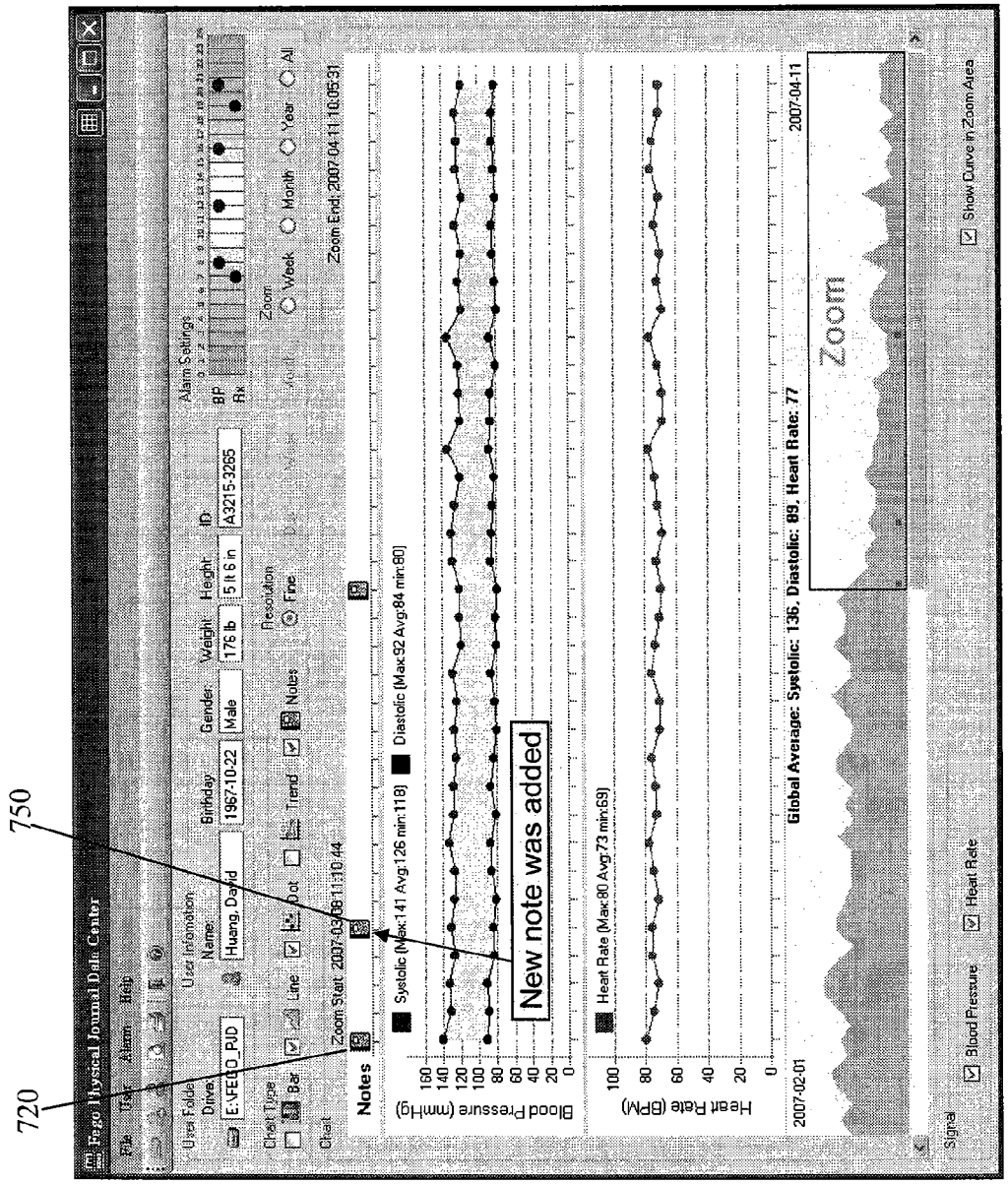

A user may add a new note at a specific date and time by clicking a specific point along the x-axis, and then input the note. As illustrated in FIG. 7C, a window (740) is popped up, and the user may add the new note using this popped up window (740). For instance, the user may type in a text note, and click the "Add Note" button to add the text note; or the user may record an audio note, replay or delete the audio note by clicking the "Record", "Play", or "Delete" buttons, respectively, in the window (740). Microsoft Office files, such as Word files, Excel files, and other applicable documents may further be added as notes corresponding to particular measuring events. These documents may be attached, viewed, or deleted by clicking the "Attach", "View", and "Delete" buttons, respectively, in the window (740). After the note is added, another icon, e.g., icon (750) will appear at the specific point along the x-axis. This greatly adds flexibility for a user to take notes with respect to each blood pressure measuring event.

Security may be applied for accessing measurement data in a measuring event and notes taken or manipulated with respect to the measuring event. The notes and/or measurement data stored may be encrypted, and a user may need to be authenticated before he/she accesses the notes and/or measurement data. For example, a user may be asked to input a user ID and a password if he/she wants to access the notes or the measurement data stored in a measurement device or an external storage device. The user may be provided with a default user ID and password when the user first uses the measurement device and may change the user ID and password any time later.

The previous description of the disclosed embodiments is provided to enable those skilled in the art to make or use the present invention. Various modifications to these embodiments will be readily apparent to those skilled in the art and generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A measurement device, with capabilities of note taking, comprising:
    at least one measurement component, adapted to perform measurement in at least one measuring event of the measurement device;
    a note control component, adapted to obtain and record at least one note that is input with respect to the at least one measuring event; and
    a Central Processing Unit (CPU), adapted to link the at least one note with the at least one measuring event.

2. The device of claim 1, further comprising at least one note input component for inputting the at least one note.

3. The device of claim 2, wherein the at least one note input component comprises at least one operational key.

4. The device of claim 1, wherein the at least one note is input from at least one note input device physically or wirelessly connected with the measurement device.

5. The device of claim 4, wherein the at least one note input device comprises a device selected from the group consisting of a computer, a keyboard, a camera, a camcorder, a microphone, a mouse, and a pen tablet.

6. The device of claim 1, wherein the at least one note is in a visual or audio format.

7. The device of claim 1, wherein the at least one note is linked with the at least one measuring event by a measuring timestamp of the at least one measuring event.

8. The device of claim 1, wherein the at least one note is stored in a data storage device connected with the measurement device.

9. The device of claim 1, wherein the measurement device comprises a health related measurement device.

10. The device of claim 1, wherein the at least one note is encrypted.

11. The device of claim 1, wherein authentication is applied to access the at least one note.

12. A method of note taking in a measurement device, comprising the steps of:
- providing means for obtaining and recording at least one note with respect to at least one measuring event of the measurement device;
- obtaining the at least one note from at least one note input means; and
- linking the at least one note with the at least one measuring event.

13. The method of claim 12, further comprising the step of encrypting the at least one note.

14. The method of claim 12, further comprising the step of storing the at least one note.

15. The method of claim 12, further comprising the step of manipulating the at least one note.

16. The method of claim 12, wherein the at least one note input means comprises a note input device physically or wirelessly connected with the measurement device.

17. The system of claim 16, wherein the note input device comprises a device selected from the group consisting of a computer, a keyboard, a camera, a camcorder, a microphone, a mouse, and a pen tablet.

18. The system of claim 12, wherein the at least one note input means comprises a built-in component of the measurement device.

19. The system of claim 12, wherein the at least one note is in a visual or audio format.

20. The system of claim 12, wherein the at least one note is linked with the at least one measuring event by a measuring timestamp of the at least one measuring event.

* * * * *